United States Patent [19]

Stand et al.

[11] Patent Number: 5,152,435
[45] Date of Patent: Oct. 6, 1992

[54] OPHTHALMIC DISPENSING PUMP

[75] Inventors: Mille Stand, Croton-on-Hudson, N.Y.; Ben Z. Cohen, 140 E. 80th St., New York, N.Y. 10021

[73] Assignee: Ben Zane Cohen, New York, N.Y.

[21] Appl. No.: 714,641

[22] Filed: Jun. 13, 1991

[51] Int. Cl.⁵ .......................................... G01F 11/06
[52] U.S. Cl. ............................... 222/321; 222/341; 222/385; 239/333; 239/590; 604/289; 604/296
[58] Field of Search ............... 222/321, 322, 341, 383, 222/385; 239/333, 590, 590.5; 604/289, 290, 296; 606/107

[56] References Cited

U.S. PATENT DOCUMENTS

| | | | |
|---|---|---|---|
| 3,167,217 | 1/1965 | Corsette et al. | 222/321 X |
| 4,140,249 | 2/1979 | Majima | 222/385 X |
| 4,185,776 | 1/1980 | Nozawa | 222/321 X |
| 4,214,682 | 7/1980 | Thomas, Jr. | 222/321 |
| 4,305,530 | 12/1981 | Nozawa | 222/321 |
| 4,606,479 | 8/1986 | Van Brocklin | 222/321 |
| 4,607,765 | 8/1986 | Ruscitti | 222/321 |
| 4,896,799 | 1/1990 | Giuffredi | 222/321 |

FOREIGN PATENT DOCUMENTS

| | | | |
|---|---|---|---|
| 729999 | 3/1966 | Canada | 222/321 |
| 3620897 | 12/1987 | Fed. Rep. of Germany | 222/321 |
| 1183465 | 1/1959 | France | 222/321 |
| 59048 | 5/1967 | German Democratic Rep. | 239/333 |
| 8204203 | 12/1982 | World Int. Prop. O. | 222/321 |

*Primary Examiner*—Andres Kashnikow
*Assistant Examiner*—Joseph A. Kaufman
*Attorney, Agent, or Firm*—Anthony J. Casella; Gerald E. Hespos

[57] ABSTRACT

A manually operated dispensing pump is provided for delivering a precise quantity of ophthalmic solution to the surface of the eye in a desired spray pattern with an impact pressure on the eye that is comfortably tolerable by an individual. The dispensing pump basically comprises a push button actuator having a nozzle member disposed therein, a cap member for receiving the push button actuator and having a control ring for selectively limiting the downward travel of the actuator, and a pump chamber engaged in the cap member and in communication with the push-button actuator for pressurizing a metered quantity of ophthalmic solution.

10 Claims, 3 Drawing Sheets

OPHTHALMIC DISPENSING PUMP

BACKGROUND OF THE INVENTION

This invention relates to a device for the delivery of therapeutic liquids from dispensing containers. In particular, the invention is directed to a spray pump for delivering a precise quantity of ophthalmic solution to the surface of the eye in a desired spray pattern at a low impact pressure. Traditionally, liquids intended to be applied to the eyes for therapeutic and related purposes have been dispensed from small flexible containers that may be squeezed to cause droplets of liquid to be introduced onto the surface of the eye. More particularly, the individual using this method of delivery must tilt their head backwards and hold the dispensing container above their eye to allow the droplets to fall under the force of gravity. This method of delivery has numerous disadvantages. In particular, there is a tendency for the tip of the dispensing container to come into contact with the surface of the eye itself, thereby possibly causing irritation or injury to the eye. Furthermore, should the tip of the dispensing container come into contact with the surface of one eye having an infection, that infection may be transferred to the other eye. In addition, this type of application of drops from a flexible squeeze bottle may result in a significant waste of liquid. In particular, when dispensing liquid from a flexible squeeze bottle up to fifty (50%) percent of the liquid delivered to the eye may not even fall on the surface thereof. Consequently, the loss of up to fifty (50%) percent of the medicinal fluid is extremely costly.

There are no known spray pumps for delivering a precise quantity of ophthalmic fluid to the surface of the eye in a spray pattern having a diameter that is approximately equal to the diameter of the pupil of the eye with an impact pressure on the eye that is comfortably tolerated by an individual.

Prior art spray pump devices for delivering liquid from a container include U.S. Pat. No. 4,140,249 entitled "MANUAL SPRAY PUMP" which issued to Majima on Feb. 20, 1979, and which discloses a manual spray pump for spraying a coarsely atomized liquid under pressure. The manual spray pump basically comprises a pump cylinder having a large piston which is movable in the axial direction therein. The piston serves to withdraw and compress the liquid from a tubular member extending from a valve tube. The spray pump disclosed in U.S. Pat. No. 4,140,249 delivers a coarsely atomized spray that may be intolerable when introduced to the surface of the eye. Therefore, it is unsuited for use in dispensing ophthalmic solution. In addition, an atomized spray pattern is likely to have a diameter that is substantially greater than the diameter of the pupil of the eye. Hence, the use of the spray pump disclosed in U.S. Pat. No. 4,140,249 may result in substantial material waste.

U.S. Pat. No. 4,185,776 entitled "MANUALLY OPERATIVE ATOMIZER" which issued to Nozawa on Jan. 29, 1980 discloses an atomizer of the accumulator type for delivering chemical agents or the like from a container. In particular, the atomizer includes a discharge valve adapted to be forced to close until a sufficiently high pressure is established. Thus, the discharge valve is never opened when the atomizer is initially depressed, but is allowed to open once a required pressure is established, so as to perform a fine atomization. The pump disclosed in U.S. Pat. No. 4,185,776 delivers a fine atomized spray under high pressure that may be intolerable when introduced to the surface of the eye.

U.S. Pat. No. 4,305,530 entitled "LIQUID ATOMIZER" which issued to Nozawa on Dec. 15, 1981 discloses a liquid pressurizing chamber for insertion into a liquid container. In particular, the atomizer comprises a cylinder for slidably receiving a body which includes three movable pistons. The liquid in the pressurizing chamber defined by the cylinder and the pistons is pressurized as the body is depressed overcoming a force of a spring. The pump disclosed in U.S. Pat. No. 4,305,530 delivers an atomized spray that is likely to have a diameter that is substantially greater than that of the eye. Therefore, the use of the pump may result in substantial material loss.

U.S. Pat. No. 4,606,479 entitled "PUMP FOR DISPENSING LIQUID, A CONTAINER" which issued to Van Brocklin on Aug. 19, 1986 discloses a pump comprising a cylinder and a piston having an interior chamber with a valve member disposed therein. In particular, the pump includes an actuator having a nozzle for dispersing liquid in a fine, aerosol spray. In operation, the pump may be used by moving the actuator through only a portion of the stroke. Therefore, the individual may vary the quantity of liquid dispersed. Furthermore, an elderly or infirm individual may have difficulty applying a partial pressure to the pump in order to dispense a desired quantity of fluid. Thus, the pump disclosed in U.S. Pat. No. 4,606,479 is unsuited for the delivery of a precise quantity of ophthalmic solution to the surface of the eye.

U.S. Pat. No. 4,607,765 entitled "MANUALLY OPERATED PUMP FOR THE DELIVERY UNDER PRESSURE OF LIQUID SUBSTANCES" which issued to Ruscitti on Aug. 26, 1986 discloses a manually operated pump for delivery under pressure in a micronized form liquid from a container. The pump comprises a main hollow body defining a movable hollow stem supporting a micronizing cap and extending into a pressure chamber. It is undesirable to deliver ophthalmic fluid to the surface of the eye in a micronized form. Therefore, the pump disclosed in U.S. Pat. No. 4,607,765 is unsuitable for dispensing ophthalmic solution.

U.S Pat. No. 4,896,799 entitled "DEVICE WITH BUTTON INCORPORATING A SHUT-OFF MEANS, FOR DELIVERING LIQUIDS IN ATOMIZED FORM" which issued to Giuffredi on Jan. 30, 1990 comprises a pump having a plunger mobile in a cylinder against the action of a spring, and a delivery button associated with the plunger for controlling its delivery movement. In particular, the button incorporates a shut-off member provided on a flexible diaphragm fixed peripherally in a seat in the button. The diaphragm is provided to enable the atomization of fluids which may atomize at different pressures. It is however, undesirable to deliver therapeutic fluids to the surface of the eye in an atomized form because of the likelihood of costly material losses.

None of the above identified prior art references is directed to a manually operated spray pump for delivering a precise quantity of liquid in a gentle stream having a desired spray pattern with a substantially low exit pressure that may be comfortably tolerated by an individual. Moreover, the quantity of liquid which may be delivered through the operation of the prior art pumps may vary depending upon the pressure exerted on the pump actuator.

Therefore, it is a primary object of the subject invention to provide a manually operated spray pump device for delivering a precise quantity of ophthalmic solution to the surface of the eye.

It is a further object of the subject invention to provide a manually operated spray pump device having means for controlling the desired quantity of ophthalmic solution to be delivered to the surface of the eye.

It is a further object of the subject invention to provide a manually operated spray pump device for delivering a precise quantity of ophthalmic solution in a precisely defined spray pattern, at a pressure not greater than that which may be comfortably tolerated by an individual.

It is a further object of the subject invention to provide a manually operated spray pump device for delivering ophthalmic solution to the surface of the eye in a manner that will reduce the quantity of material wasted during applications a compared to a conventional squeeze bottle.

It is a further object of the subject invention to provide a manually operated spray pump device for delivering ophthalmic solution to the surface of the eye that is substantially more accurate than a conventional squeeze bottle in delivering solution to the surface of the eye.

It is a further object of the invention to provide a manually operated spray pump apparatus capable of selectively altering the dosage of ophthalmic solution to be dispensed with each actuation.

SUMMARY OF THE INVENTION

The ophthalmic dispensing pump of the subject invention is provided for delivering ophthalmic solution to the surface of the eye. In particular, the manually operated dispensing pump will enable an individual to deliver a precise quantity of ophthalmic solution to the surface of the individual's eye in a desired spray pattern with an impact pressure on the eye that is not greater than that which may be comfortably tolerated by the individual. The ophthalmic dispensing pump of the subject invention basically comprises a pump chamber, a push button actuator, a cap member and a container accommodating ophthalmic solution.

The pump chamber of the subject ophthalmic dispensing pump may have an elongated hollow body with a stepped outer wall dimensioned to be press fit in the neck of the dispenser container. A cylindrical tube member is slidably movable within the pump chamber and may be biased against a plunger by a coiled spring. The pump chamber may further include valving means for regulating the flow of ophthalmic solution therethrough. The cylindrical tube member of the pump chamber may be received in an axially aligned cylindrical recess formed in the push button actuator so that the tube member and the push button actuator move in unison. A transversely aligned elongated aperture may be formed in the push button actuator and in communication with the cylindrical recess formed therein. The transversely aligned aperture in the push button actuator may be formed with a parabolic shaped rear wall. A nozzle member may be engaged in the transversely aligned elongated aperture. The nozzle member may be provided with a venturi shaped passageway extending therethrough. The venturi passageway is configured and dimensioned to deliver the ophthalmic solution to the eye in a precisely defined pattern and at a pressure not greater than that which may be comfortably tolerated by an individual. The pump chamber and the actuator both may be received in the cap member. Furthermore, limiting means may be disposed within the cap member for limiting the travel of the actuator into the cap member during operation of the ophthalmic spray pump, and thereby precisely controlling the dispensed dosage.

In operation, the actuator may be depressed such that the cylindrical tube member of the pump chamber is slidably received therein. At such a time, a metered quantity of ophthalmic solution is compressed in the cylindrical tube member of the pump chamber, thereby causing the valving means disposed therein to open. Thereupon, a desired quantity of ophthalmic solution that has been accumulated in the elongated aperture of the actuator may exit the dispensing pump through the venturi shaped passageway in the nozzle member. Subsequently, the actuator may be released so that it may return to its initial rest condition under the influence of the coiled spring. At such a time, decompression occurs within the cylindrical tube member of the pump chamber, thereby causing the valving means disposed therein to open. Thereupon, ophthalmic solution may be drawn into the pump chamber from the container.

DETAILED DESCRIPTION OF THE PREFERRED EMBODIMENT

Figure 1:
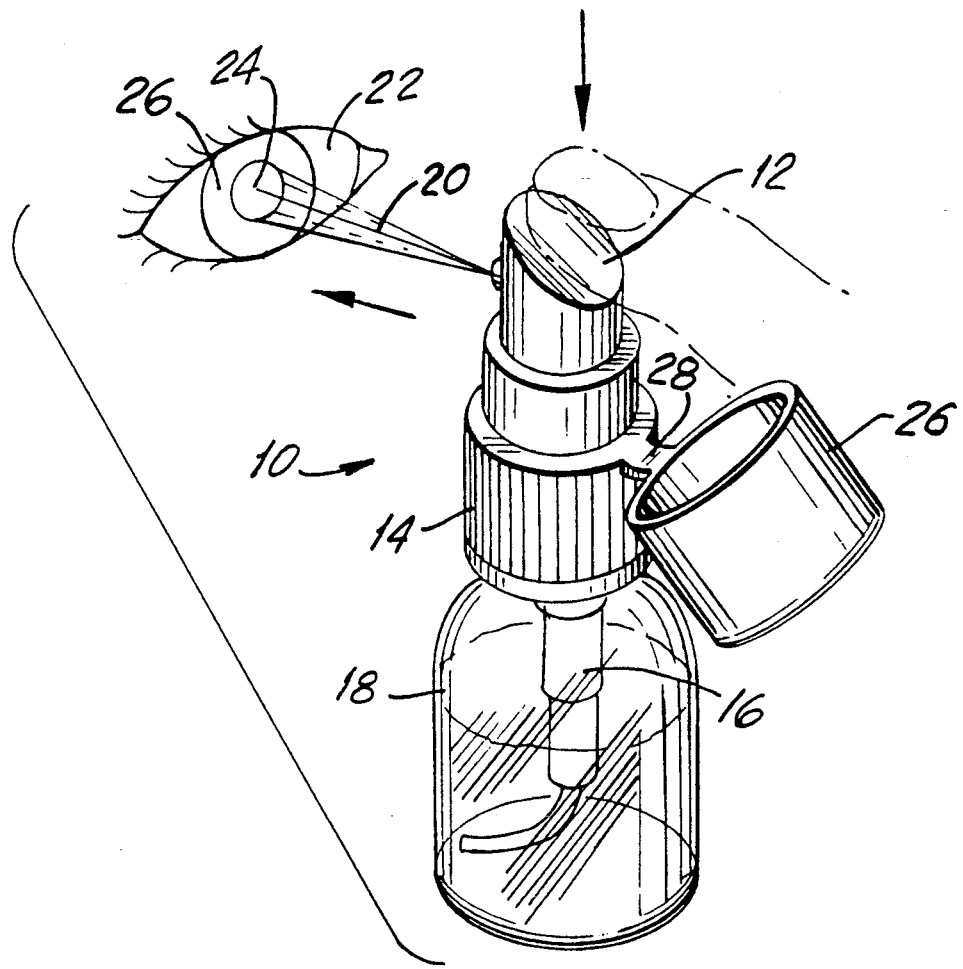
FIG. 1 is a perspective view of the ophthalmic dispensing pump of the subject invention.

The ophthalmic dispensing pump of the subject invention is illustrated in FIG. 1 and is designated generally by reference numeral 10. The dispensing pump 10 basically comprises a generally cylindrical push button actuator 12, a mounting cap 14 for receiving the actuator 12 and a pump chamber 16 in communication with the actuator 12 which may be press fit into a dispensing container 18 containing ophthalmic solution. The dispensing pump 10 of the subject invention is provided to enable an operator to deliver a precise quantity of ophthalmic solution to the surface of his/her eye 20. Moreover, the spray pump 10 will deliver a metered volume of fluid to the surface of the eye 20 in a desired spray pattern 22 with an impact pressure that may be comfortably tolerated by an individual.

Referring to FIG. I, the ophthalmic dispensing pump 10 further comprises a dust cover 26 that is hingedly connected to the mounting cap 24 by a flexible hinge 28. The dust cover 26 is provided to be fitted over the actuator 12 in order to prevent contaminates which may cause infections in the eye from being deposited thereon.

Figures 2, 3:
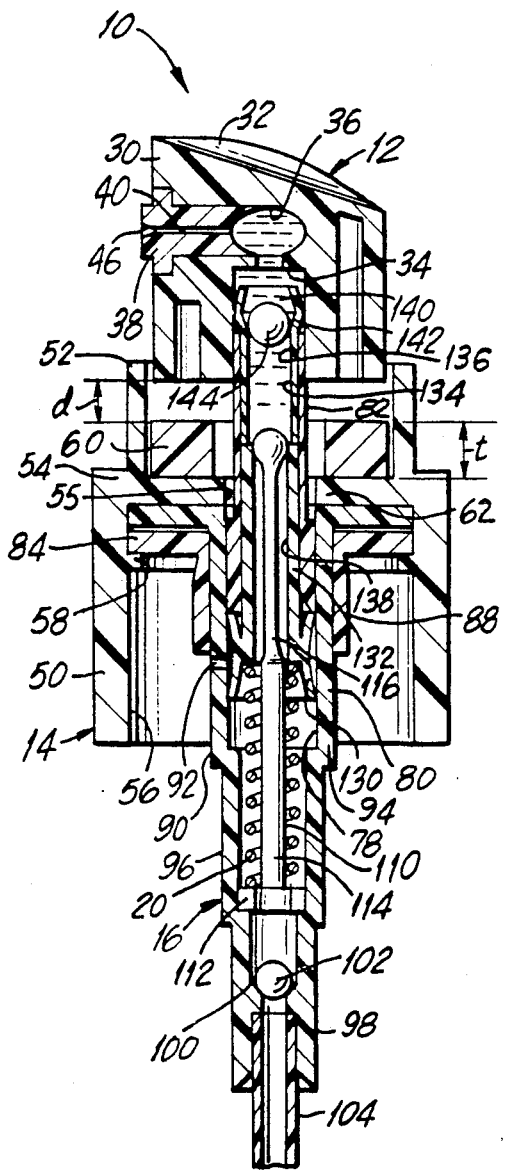
FIG. 2 is a cross-sectional view of the ophthalmic dispensing pump of the subject invention in its initial rest position.
FIG. 3 is a cross-sectional view of the ophthalmic dispensing pump of the subject invention in the partially depressed position wherein liquid is dispensed.

Referring to FIG. 2, the ophthalmic dispensing pump 10 of the subject invention is illustrated in its initial rest condition. The push button actuator 12 of the spray pump 10 of the subject invention is defined by a generally cylindrical outer wall 30, an upper surface 32 for finger actuation and a cylindrical recess 34 for receiving the pump chamber 16. The actuator 12 is provided with a parabolic duct 36 in which a desired volume of fluid is retained prior to being dispensed. The parabolic duct 36 is part of the ovoid chamber shown in FIGS. 2–5. The focal point of the parabolic duct 36 is disposed on the longitudinal centerline of the actuator 12. The actuator 12 further includes a nozzle member 38 which is force fit into the outer wall 30 thereof.

The nozzle member 38 is formed with a venturi shaped passageway 40 extending therethrough and defined by an ovoid shaped inlet port 42, which converges into a cylindrical bore 44 having a diameter of about 0.4 mm, and a diverging conical shaped outlet port 46. The venturi shaped passageway 40 formed in the nozzle member 38 is intended to limit the generation of turbulence in the fluid as it is compressed therein during the operation of the spray pump 10 of the subject invention. Therefore, the fluid entering the inlet port 42 remains in a laminar condition as it passes through the cylindrical bore 44 such that upon exiting the outlet port 46 it will remain in a precise stream like pattern 22. More particularly, the periphery of the outlet port 46 is formed with a diverging wall having an angle of divergence $\alpha$ in the general range of 8°–11° such that the exiting fluid stream 22 has a diameter that is in the range of 7 mm–14 mm, which is between the typical diameter of 8 mm for the pupil 24 and the typical diameter of 25 mm for the cornea 26 of the individual's eye 20. Furthermore, when dispensing pump 10 is held 1.0 to 1.5 inches from the individual's eye the fluid stream 22 has a considerably low impact pressure that is between 2.75 and 6.80 mmHg, thereby ensuring that the exiting fluid stream 22 will make gentle contact with the surface of the eye 20 so as not to cause discomfort to an individual.

The mounting cap 14 of the dispensing pump 10 of the subject invention is defined by a generally cylindrical lower portion 50 for receiving the neck 48 of the dispenser container 18, a cylindrical upper portion 52 for receiving the actuator 12 during operation of the spray pump 10, and a medial inner wall 54 with a circular aperture 55 separating the lower portion 50 from the upper portion 52. The inner surface 56 of the lower portion 50 of the mounting cap 14 is provided with a pair of radially projecting flanges 58 for engaging the pump chamber 16. Disposed in the upper portion 52 of the mounting cap 14 is a removable control ring 60.

The removable control ring 60 includes an axial aperture 62 and is provided to limit the downward travel of the push button actuator 12 such that the amount of fluid that is dispensed from the spray pump 10 upon each operation is of a precise metered quantity. Moreover, the thickness "t" of the control ring 60 may be selectively varied such that the distance of downward travel "d" of the actuator 12 may be varied. Consequently, the spray pump 10 may be used to dispense any required volume of fluid by merely installing a control ring 60 of a desired thickness "t". In the preferred embodiment of the spray pump 10 of the subject invention the thickness "t" of the control ring 60 is selected to permit the delivery of precisely 0.05 ml of ophthalmic solution to the surface of the eye 20, which is the volume of fluid in a standard droplet of ophthalmic solution that is delivered from a conventional flexible squeeze bottle.

The pump chamber 16 of the spray pump 10 of the subject invention is basically defined by an elongated hollow body 80 having a stepped axial bore 78 extending therethrough and having an elongated pressure chamber 82 slidably movable therein. The hollow body 80 includes a retaining ring 84 disposed on the upper distal end thereof for inter-engagement with the annular locking flange 58 disposed on the inner surface 56 of the lower portion 50 of the mounting cap 14. Adjacent to the retaining ring 84 is a dispenser container engaging portion 88 having an outer diameter that is suitable to be press fit into the neck 48 of an ophthalmic dispenser container 18. Immediately below engagement portion 88 of the pump chamber 16 is a first intermediate portion 90 having a vent 92 extending through the side wall 94 thereof for allowing the exit of air that may become trapped within the pump chamber 16 during operation of the spray pump 10 of the subject invention. Immediately adjacent to the first intermediate portion 90 is a second intermediate portion 96 from which extends end portion 98 of the pump chamber 16. End portion 98 includes a valve seat 100 disposed adjacent the distal end thereof in which a ball type check valve 102 is seated for regulating the flow of fluid therethrough. Extended into the end portion 98 is an elongated dip tube 104 that is curved at the lower end thereof (see FIG. 1), through which ophthalmic solution may be drawn during the operation of the spray pump 10 of the subject invention.

The pump chamber 16 is further provided with a plunger 110 disposed in the axial bore 78 thereof. The plunger 110 includes a base portion 112 seated in the bottom of the second intermediate portion 96 of the pump chamber 16, an elongated shaft portion 114, an elongated neck portion 116 and a generally spherical head portion 118. A coiled spring 120 is disposed on the shaft portion 114 of the plunger 110 which is compressed during actuation of the push button actuator 12 of the spray pump 10 of the subject invention.

The elongated pressure chamber 82 includes a lower frustum shaped cup 130 and an elongated body 132 having a stepped axial bore 134 defined by a lower portion 136 and an upper metering portion 138. The upper portion of the coiled spring 120 is firmly fit into the frustum shaped cup 130. The pressure chamber 82 further includes an upper cup portion 140 which is provided with a valve seat 142 in which is disposed a ball type check valve 144 for regulating the flow of fluid therethrough. The elongated neck portion of the plunger 110 extends through the lower portion 136 of the axial bore 134 such that the spherical head 118 of the plunger 110 is positioned within the upper metering portion 138 of the axial bore 134.

Referring to FIG. 3, in operation, once the spray pump 10 of the subject invention has been primed, a downwardly applied force "F" may be exerted on the upper surface 32 of the push button actuator 12 such that the push button actuator 12 travels downward into the upper portion 52 of the mounting cap 14. At such a time, the pressure chamber 82 extends into the first intermediate portion 90 of the pump chamber 16 causing the coiled spring 120 to compress. Thereupon, fluid 122 that has been retained in the upper metering portion 138 of axial bore 134 of the pressure chamber 82 forces the check valve to rise under the increased pressure gradient caused by the change in volume in the upper metering portion 138. The subsequent change in pressure in the parabolic duct 36 causes the laminar flow of ophthalmic solution through the venturi shaped passageway 40 in the nozzle member 38 and the dispensing of the ophthalmic solution in a gentle stream 22 having a diameter which is between the diameters of the pupil 24 and the cornea 26 of the eye 20. During the downstroke operation of the spray pump 10 of the subject invention the actuator 12 may only travel a distance "d", whereby a desired quantity of ophthalmic solution may be delivered to the surface of the eye 20. The distance of travel "d" is limited by the thickness "t" of the removable control ring 60 disposed in the upper portion 52 of the mounting cap 14.

Figure 4:
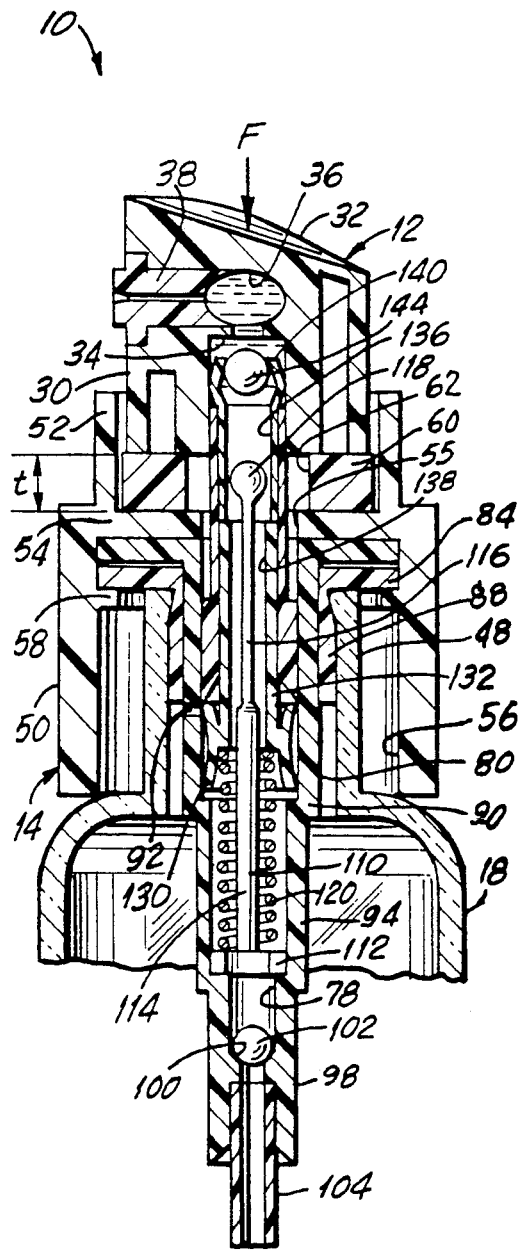
FIG. 4 is a cross-sectional view of the ophthalmic dispensing pump of the subject invention wherein the actuator button is fully depressed.

Referring to FIG. 4, the downward travel of the actuator 12 is stopped by the control ring 60. At such a time, the ball type check valve 144 is in its fully raised position in the upper cup portion 140 of the pressure chamber 82. Thereupon, the finger pressure on the upper surface face 32 of the actuator 12 may be released.

Figure 5:
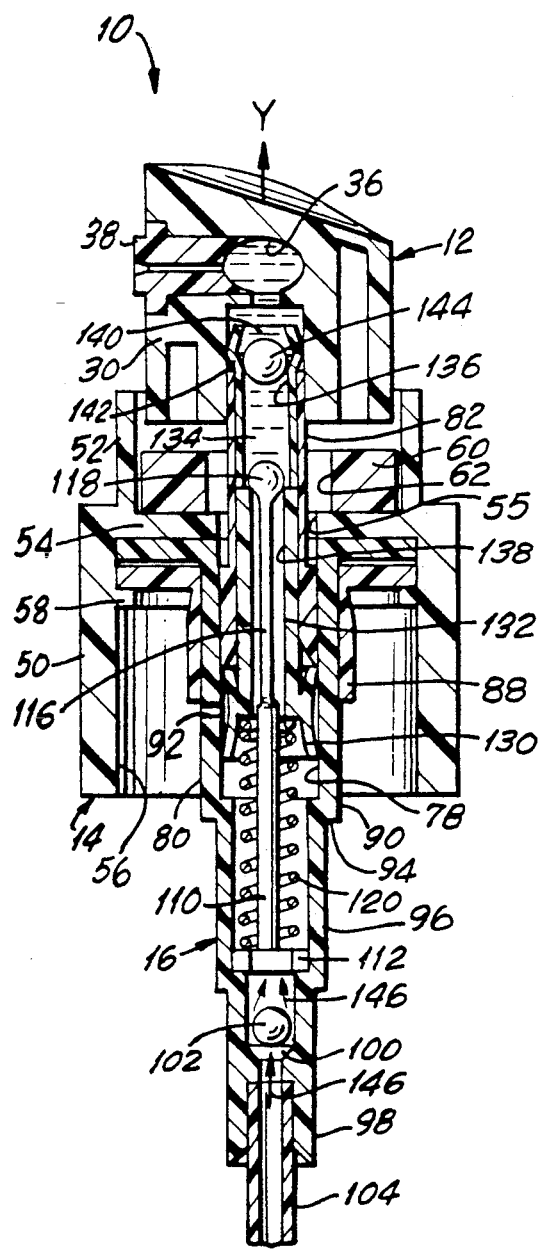
FIG. 5 is a cross-sectional view of the ophthalmic dispensing pump of the subject invention in a position wherein liquid is being suctioned from the container.

Referring to FIG. 5, upon releasing the actuator button 12 of the spray pump 10 of the subject invention the coiled spring 120 may return to its relaxed condition thereby causing the pressure chamber 82 to slidably exit the intermediate portion 90 of the pump chamber 16 in the direction of force line "Y". At such a time, air which may have been drawn into the axial bore 78 of the pump chamber 16 as a result of the change in pressure therein is forced out of the vent 92 in the side wall 94 thereof. Subsequently, there is a change in pressure differential within the pump chamber 16 caused by the increase in volume of the upper metering portion 138 of the axial bore 134 of the pressure chamber 82 resulting from the upward travel of the actuator 12. This subsequent change in pressure causes the ball type check valve 102 within the end portion 98 of the pump chamber to rise from the valve seat 100. Thereafter, ophthalmic solution 146 may drawn into the spray pump 10 of the subject invention through the dip tube 104 from the dispenser container 18 until the pressure within the pump chamber 16 is neutralized. Thereupon, the ball type check valve 102 may return to its closed condition in the valve seat 100.

In summary, a spray pump is provided for delivering ophthalmic solution to the surface of the eye comprising a manually operated actuator having a venturi shaped nozzle, a mounting cap for receiving the actuator having means for limiting the downward travel thereof and a pump chamber for compressing fluid in communication with the actuator. In particular, the spray pump is provided to enable an operator to deliver a precise quantity of ophthalmic solution to the surface of his/her eye. Moreover, the spray pump will deliver a metered volume of fluid in a precise spray pattern with an impact pressure that is comfortably tolerable by an individual.

While the invention has been described with respect to a preferred embodiment, it is apparent that modifications can be made without departing from the spirit and scope of the invention as defined by the appended claims. In particular, bottles with shapes and dimensions different from those depicted herein may be employed with the subject dispensing pump. Furthermore, the spring characteristics may be changed in accordance with the viscosity of the solution being dispensed.

We claim:

1. A manually operated dispensing pump for delivering a precise quantity of ophthalmic solution to the surface of the eye in a desired spray pattern with an impact pressure on the eye that is comfortably tolerated by an individual, said dispensing pump comprising;
    a container having a closed bottom for accommodating ophthalmic solution and an opened top defining a neck;
    an elongated hollow pump body having an upper end mounted to the neck of said container and a lower end disposed in said container;
    a cap mounted to the upper end of the pump body, the cap having opposed top and bottom ends and an aperture extending axially therebetween substantially in alignment with the pump body, said top end of said cap extending upwardly beyond the neck of the container and being formed with an axially aligned actuator recess therein;
    a tube slidably movable in said pump body and having opposed upper and lower ends, the upper end projecting through the aperture in said cap;
    valving means mounted to the tube and the pump body for urging ophthalmic solution upwardly through the tube in response to a downward movement of the tube in the pump body, the quantity of the ophthalmic solution urged through the tube being a function of the distance of travel of the tube in the pump body;
    an actuator with a bottom end slidably disposed in the actuator recess of the cap, an elongated axial bore extending into the bottom end of the actuator, the top end of the tube being engaged in the axial bore of the actuator such that the actuator and the tube are moveable substantially in unison, an elongated recess extending into the actuator transverse to the axial bore, an ovoid chamber defined in the actuator and providing communication between the axial bore and the recess, the ovoid chamber being at least partly defined by a generally parabolic wall disposed generally opposite the recess, the actuator being dimensioned to permit a downward movement in the actuator recess of the cap for urging the precise quantity of the ophthalmic solution through the tube; and
    a nozzle fixed in said recess of said actuator and including a concave generally ovoid inlet port in communication with the ovoid chamber of the actuator, a concave generally conical outlet port external of said actuator and a venturi shaped passageway extending therebetween, with said parabolic wall of said ovoid chamber being aligned with the longitudinal axis of said venturi shaped passageway, and wherein said concave ovoid inlet port has an angle of convergence that is greater than the angle of divergence of said conical wall of said outlet port whereby said ovoid chamber, said venturi shaped passageway, and said outlet port are dimensioned and configured to generate a narrow stream of the ophthalmic solution in response to a downward movement of the actuator in the actuator recess of the cap.

2. A manually operated dispensing pump as in claim 1 wherein said conical wall of said outlet port diverges at an angle in the range of between 8° and 11° from the longitudinal axis thereof.

3. A manually operated spray pump as in claim 1 wherein a dust cover is hingedly connected to said cap for covering the actuator body.

4. A manually operated spray pump as in claim 1, wherein the precise quantity of ophthalmic solution defines a maximum dosage, and wherein said pump further comprises a limiting means disposed in the actuator recess of said cap for limiting the downward movement of said actuator in said actuator recess, the limiting means being dimensioned to define a specified dosage less than the maximum dosage in response to the downward movement of the actuator in the actuator recess.

5. A manually operated dispensing pump as in claim 4, wherein said limiting means comprises an annular ring disposed in said actuator recess and surrounding an upper end of the tube.

6. A manually operated spray pump as in claim 1, wherein the passageway in the nozzle has a diameter of approximately 0.4 mm.

7. A manually operated dispensing pump as in claim 1, wherein the passageway in the nozzle and the outlet port thereof are configured to generate a fluid stream approximately 7 mm-14 mm in diameter and an impact pressure of between 2.75-6.8 mmHg at a distance of between 1.0-1.5 inches for avoiding damage and discomfort to an eye of a patient.

8. A manually operated dispensing pump for delivering a precise quantity of ophthalmic solution to the surface of the eye in a desired spray pattern with an impact pressure on the eye that is comfortably tolerated by an individual, said dispensing pump comprising:

a container having a closed bottom for accommodating ophthalmic solution and an opened top defining a neck;

an elongated hollow pump body having an upper end mounted to the neck of said container and a lower end disposed in said container;

a cap mounted to the upper end of the pump body, the cap having opposed top and bottom ends and an aperture extending axially therebetween substantially in alignment with the pump body, said top end of said cap extending upwardly beyond the neck of the container and being formed with an axially aligned actuator recess therein;

a tube slidably movable in said pump body and having opposed upper and lower ends, the upper end projecting through the aperture in said cap;

valving means mounted to the tube and the pump body for urging ophthalmic solution upwardly through the tube in response to a downward movement of the tube in the pump body, the quantity of the ophthalmic solution urged through the tube being a function of the distance of travel of the tube in the pump body;

an actuator with a bottom end slidably disposed in the actuator recess of the cap, an elongated axial bore extending into the bottom end of the actuator, the top end of the tube being engaged in the axial bore of the actuator such that the actuator and the tube are moveable substantially in unison, an elongated recess extending into the actuator transverse to the axial bore, an ovoid chamber defined in the actuator and providing communication between the axial bore and the recess;

removable limiting means disposed in the actuator recess intermediate the cap and the actuator, said limiting means being dimensioned for defining a range of movement of the actuator in the actuator recess for urging the precise quantity of the ophthalmic solution through the tube; and a nozzle fixed in said recess of said actuator and including a concave inlet port in communication with the ovoid chamber of the actuator, a concave generally conical outlet port external of said actuator and a venturi shaped passageway therebetween, said ovoid chamber having a generally parabolic wall disposed generally opposite said concave inlet port and generally aligned with the longitudinal axis of said venturi shaped passageway, and with the angle of convergence of said inlet port being greater than the angle of divergence of said outlet port, whereby said ovoid chamber, said venturi shaped passageway and sad outlet port are dimensioned and configured to generate a laminar flow of a narrow stream of the ophthalmic solution in response to a downward movement of the actuator in the actuator recess of the cap.

9. A manually operated dispensing pump as in claim 8 wherein the conical wall of the outlet port diverges at an angle of between approximately 8°-11° from the longitudinal axis of the conical wall.

10. A manually operated dispensing pump as in claim 8 wherein a dust cover is hingedly connected to said cap for covering the actuator body.

* * * * *